United States Patent [19]

Okamoto et al.

[11] Patent Number: 4,585,789
[45] Date of Patent: Apr. 29, 1986

[54] NEW FURANONE DERIVATIVES, PROCESS FOR PREPARATION THEREOF AND USE THEREOF

[75] Inventors: Masanori Okamoto, Osaka; Itsuo Uchida, Kyoto; Kazuyoshi Umehara, Ashiya; Masanobu Kohsaka, Sakai; Hiroshi Imanaka, Osaka, all of Japan

[73] Assignee: Fujisawa Pharmaceutical Co., Ltd., Osaka, Japan

[21] Appl. No.: 508,892

[22] Filed: Jun. 29, 1983

[30] Foreign Application Priority Data

Jul. 19, 1982 [JP] Japan .................. 57-126599

[51] Int. Cl.[4] .................. C07D 307/32; C07D 307/60; A61K 31/34
[52] U.S. Cl. .................. 514/461; 514/473; 549/313; 549/318; 549/321
[58] Field of Search .............. 549/315, 317, 318, 321, 549/322, 323, 324; 424/279; 514/473, 461

[56] References Cited

U.S. PATENT DOCUMENTS

| | | | |
|---|---|---|---|
| 2,841,594 | 7/1958 | Lacey | 549/322 |
| 3,113,939 | 12/1963 | Martin | 549/318 |
| 3,509,209 | 4/1970 | Fenton | 549/322 |
| 3,564,020 | 2/1971 | Fenton | 549/322 |
| 3,665,014 | 5/1972 | Fauran et al. | 549/323 |
| 3,813,416 | 5/1974 | Heiba et al. | 549/323 |
| 3,838,168 | 9/1974 | Parker et al. | 549/321 |
| 3,873,575 | 3/1975 | Semonsky et al. | 549/323 |
| 3,940,424 | 2/1976 | Lannert | 549/322 |
| 4,010,170 | 3/1977 | Larock | 549/324 |
| 4,214,092 | 7/1980 | Kraus | 549/322 |
| 4,508,914 | 4/1985 | Schmidt | 549/323 |

FOREIGN PATENT DOCUMENTS

| 1920176 | 10/1970 | Fed. Rep. of Germany | 549/321 |
|---|---|---|---|
| 44-27027 | 11/1969 | Japan | 549/324 |

OTHER PUBLICATIONS

Veprek-Bilenski et al; Helvetica Chimica Acta, vol. 61, No. 8, pp. 3018-3027 (1978) Zur Reakionsweise von Diphenylcylopropen.
Brownbridge et al; Tetrahedron Letters, vol. 21, pp. 3431-3434 (1980) Chemistry of 2,5-Bis(trimethylsiloxy) Furans III.
Judzewitsch et al; New England Journal of Medicine, vol. 308, No. 3, pp. 119-125 (1983) Aldose Reductance Inhibition Improves Nerve Conduction.
Kador et al; Molecular Pharmacology, vol. 24, pp. 521-531 (1983) Pharmacophor Requirements of the Aldose Reductase Inhibitor Site.
CA: 94:65076q—Takei et al, Reaction of αBrine, α,- β-Unsaturated Esters etc., 1980.
Chemical Abstracts, vol. 93, No. 9, Sep. 1980, p. 497, Abstract 93533j.

*Primary Examiner*—Glennon H. Hollrah
*Assistant Examiner*—Dara L. Dinner
*Attorney, Agent, or Firm*—Oblon, Fisher, Spivak, McClelland & Maier

[57] ABSTRACT

Described are compounds of the formula:

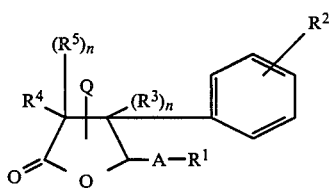

Wherein
A is a lower alkylene group;
$R^1$ is a carboxy, hydroxy, lower alkoxycarbonyl, lower alkoxycarbonylamino, phenyl(lower)alkyloxy, benzoyloxy or lower alkanoyloxy group;
$R^2$ is a hydrogen or halogen atom or a halo(lower)alkyl group;
$R^3$ is a hydrogen or halogen atom;
$R^4$ is hydroxy, lower alkoxy, lower alkanoyloxy or lower alkoxycarbonyloxy group; and
$R^5$ is a hydrogen or halogen atom;
Q is the number of double bonds which is equal to 0 or 1;
n is an integer of 0 or 1, provided that when Q is 0, n is 1 and when Q is 1, n is 0.

4 Claims, No Drawings

NEW FURANONE DERIVATIVES, PROCESS FOR PREPARATION THEREOF AND USE THEREOF

This invention relates to new furanone derivatives. More particularly, this invention relates to new furanone derivatives and their pharmaceutically acceptable salts which have an aldose reductase-inhibitory activity, to processes for preparation thereof, and to a pharmaceutical composition comprising the same and a method of use thereof.

The new furanone derivatives of this invention can be represented by the following formula (I).

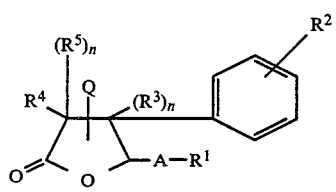

(I)

wherein A is a lower alkylene group; $R^1$ is a carboxy, hydroxy, protected hydroxy, lower alkoxycarbonyl, lower alkoxycarbornyl, lower alkoxycarbonylamino or lower alkanoyloxy group; $R^2$ is a hydrogen or halogen atom or a halo(lower)alkyl group; $R^3$ is a hydrogen or halogen atom; $R^4$ is a hydrogen atom or a hydroxy, carboxy, lower alkoxy, lower alkanoyloxy or lower alkoxycarbonyloxy group and $R^5$ is a hydrogen or halogen atom, or $R^4$ and $R^5$ are taken together to form a group: $=CH_2$; Q is the number of double bonds which is equal to 0 or 1; n is an integer of 0 or 1, provided that when Q is 0, n is 1 and when Q is 1, n is 0.

Particulars of the various definitions, which are mentioned hereinabove and hereinafter, and preferred examples thereof are explained in the following.

The term "lower" means a group of 1 to 5 carbon atoms unless otherwise specified.

(1) Re. Lower alkylene group for A and A':

Preferred examples of the alkylene group may include methylene, ethylene, trimethylene, propylene and the like.

(2) Re Lower alkoxycarbonyl group for $R^1$ and $R_a{}^4$; the lower alkoxycarbonyl moiety of lower alkoxycarbonylamino group for $R^1$; and the lower alkoxycarbonyl moiety of lower alkoxycarbonyloxy group for $R^4$:

Preferred examples of the lower alkoxycarbonyl group or moieties may include methoxycarbonyl, ethoxycarbonyl, propoxycarbonyl, butoxycarbonyl and the like.

(3) Re. Hydroxy protective group in protected hydroxy group for $R^1$; and hydroxy protective group for $R_9{}^1$ and $R_b{}^1$:

Preferred examples of the hydroxy protective group may include substituted or unsubstituted alkanoyl (e.g. formyl, acetyl, propionyl, etc.), substituted or unsubstituted aroyl (e.g. benzoyl, etc.), aralkyl (e.g. benzyl, etc.) and the like.

(4) Re. Lower alkanoyloxy group for $R^1$ and $R^4$:

Preferred examples of the lower alkanoyloxy group may include acetoxy, propionyloxy, butyryloxy, isobutyryloxy and the like.

(5) Re. Halogen atom for $R^2$, $R^3$, $R^5$, $R_9{}^5$ and $R_a{}^3$:

Preferred examples of the halogen may include chlorine, bromine, iodine and the like.

(6) Re. Halo(lower)alkyl group for $R^2$:

Preferred examples of the halo(lower)alkyl group may include chloromethyl, bromomethyl, dichloromethyl, 2,2,2-trichloroethyl, trifluoromethyl and the like. (7) Re. Lower alkanoyloxy group for $R_b{}^4$, $R_d{}^4$, $R_c{}^1$ and $R_c{}^4$:

Preferred examples of the alkanoyloxy group may include formyl, acetyl, propionyl, butyryl and the like.

(8) Re. Lower alkyl group for $R_d{}^4$, $R_d{}^1$ and $R_e{}^4$:

Preferred examples of the lower alkyl group may include methyl, ethyl, propyl, isopropyl, butyl and the like.

(9) Re. Lower alkoxy group for $R^4$:

Preferred examples of the lower alkoxy group may include methoxy, ethoxy, propoxy and the like.

(10) Re. Pharmaceutically acceptable salts of the compound (I):

Preferred examples of the pharmaceutically acceptable salts of the compound (I) may include alkali metal salts (e.g. sodium salt, potassium salt, etc.), alkaline earth metal salts (e.g. calcium salt, etc.), ammonium salt, ethanolamine salt, triethylamine salt, dicyclohexylamine salt and the like.

The new furanone derivatives (I) and pharmaceutically acceptable salt thereof can be prepared by the following processes.

(1) Process 1

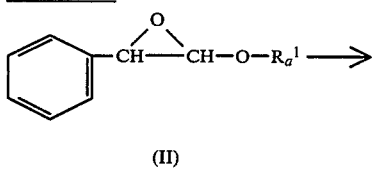

(II)

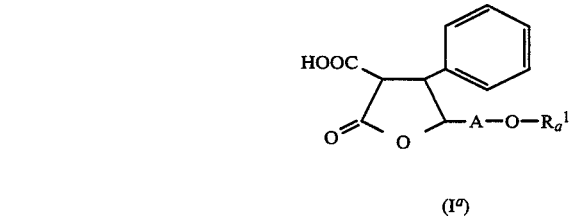

(I$^a$)

(2) Process 2

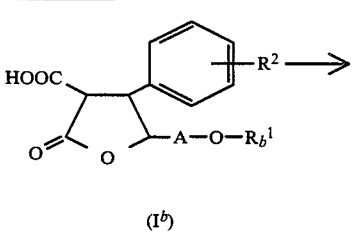

(I$^b$)

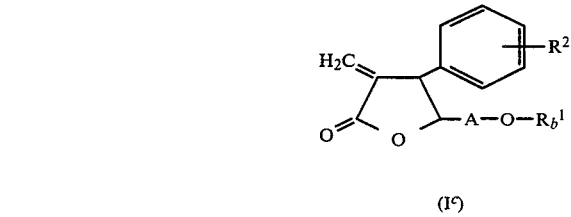

(I$^c$)

(3) Process 3

-continued
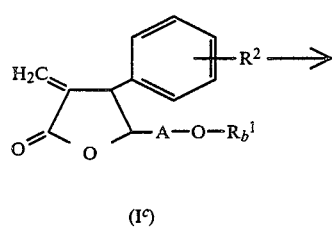
(I^c)
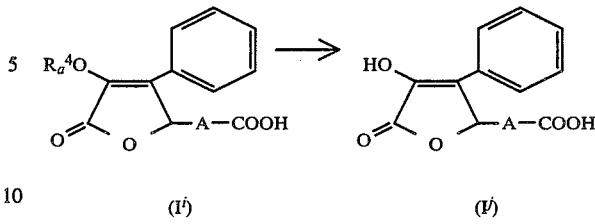
(I^i)    (I^j)
(8) Process 8
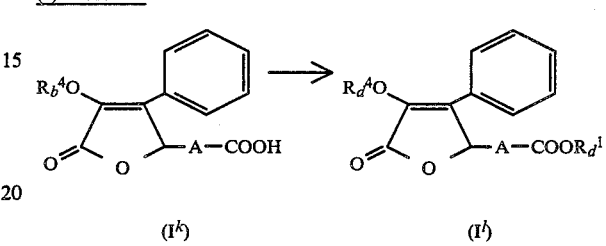
(I^k)    (I^l)
(4) Process 4
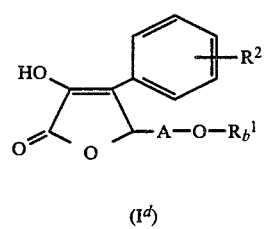
(I^e)
(9) Process 9
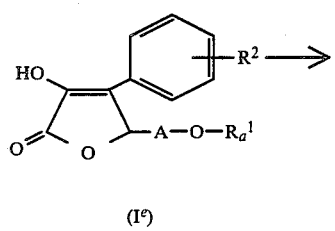
(I^d)
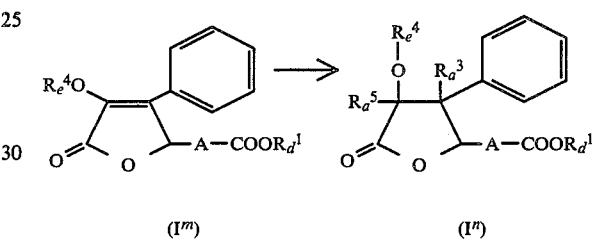
(I^m)    (I^n)
(10) Process 10
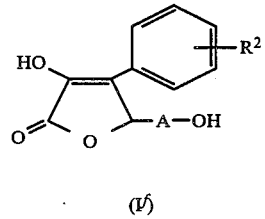
(I^f)
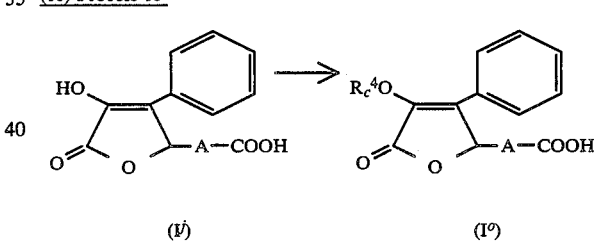
(I^j)    (I^o)
(5) Process 5
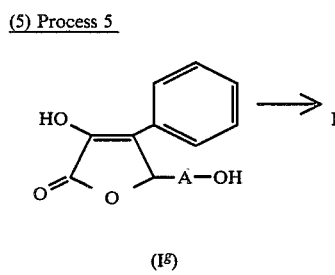
(I^g)    (I^h)
(11) Process 11
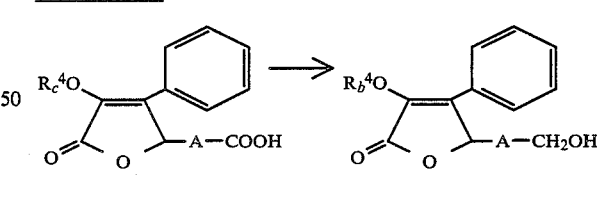
(I^o)    (I^p)
(6) Process 6
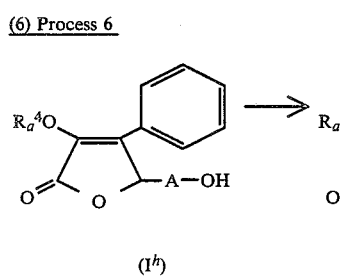
(I^h)    (I^i)
(12) Process 12
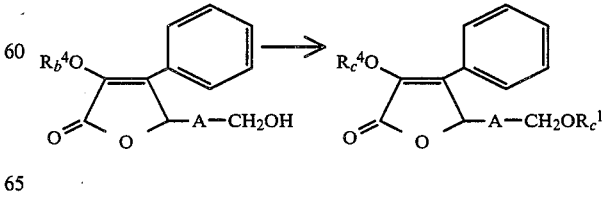
(I^p)    (I^q)
(7) Process 7
(13) Process 13

-continued

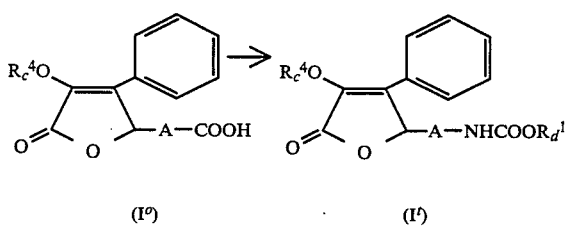

(I^o) (I^t)

(14) Process 14

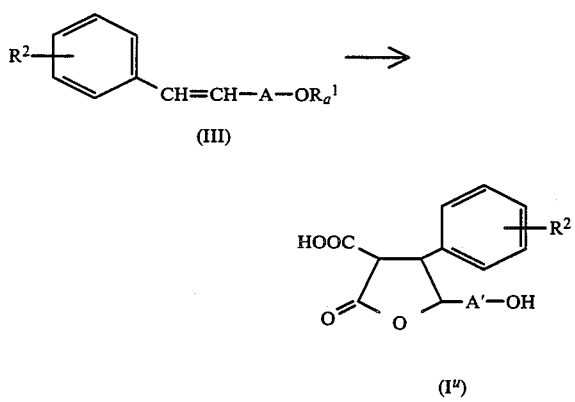

(15) Process 15

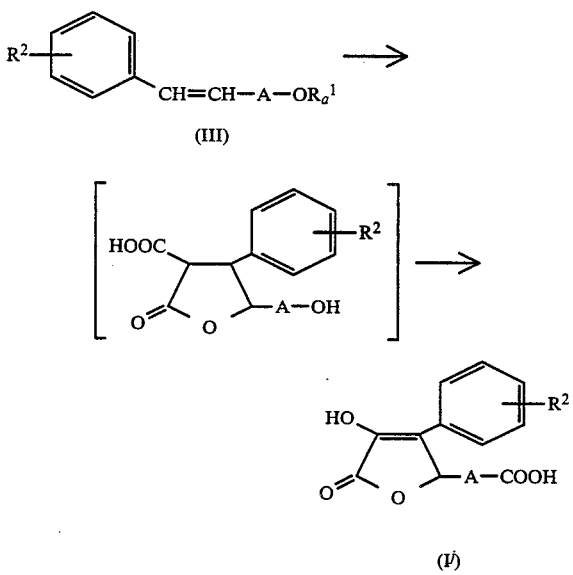

(16) Fermentation process

A microorganism belonging ⟶
to the genus Chaetomella

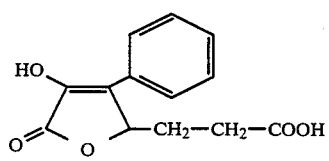

FR-51785 substance wherein $R_a^1$ is a hydroxy protective group,
$R_b^1$ is a hydrogen atom or a hydroxy protective group,
$R_a^4$ is a lower alkoxycarbonyl group,
$A'$ is a lower alkylene group,
$R_b^4$ is a hydrogen atom or a lower alkanoyl group,
$R_d^4$ is a lower alkyl group or a lower alkanoyl group,
$R_d^1$ is a lower alkyl group,
$R_c^1$ is a lower alkanoyl group,
$R_c^4$ is a lower alkanoyl group,
$R_e^4$ is a lower alkyl group,
$R_a^5$ is a halogen atom,
$R_a^3$ is a halogen atom, and
A and $R^2$ are each as defined above.

The above processes are explained in detail in the following.

(1) Process 1

The compound ($I^a$) can be prepared by reacting the compound (II) with malonic acid or its derivative at the carboxy groups in the presence of a base.

Preferred examples of the malonic acid derivative at the carboxy groups may include esters (e.g. alkyl esters such as methyl ester, ethyl ester, and propyl ester, aralkyl esters such as benzyl ester, etc.), acid amides (e.g. N-alkyl acid amides such as N-methyl acid amide and N-ethyl acid amide, etc.).

Preferred examples of the base may include alkali and alkaline earth metal hydroxides, carbonates or bicarbonates (e.g. sodium hydroxide, potassium hydroxide, calcium hydroxide, sodium carbonate, calcium carbonate, sodium bicarbonate, etc.), ammonium hydroxide, amines (e.g. methylamine, ethylamine, diethylamine, trimethylamine, etc.) and the like.

This reaction is preferably conducted in a solvent inert to the reaction, such as methanol, ethanol, or propanol, at ambient temperature or under heating up to the refluxing temperature.

(2) Process 2

The compound ($I^c$) can be prepared by reacting the compound ($I^b$) or its salt with formalin in the presence of a base.

Preferred examples of salts of the compound ($I^b$) may include the same as those of the compound (I).

Preferred examples of the base are the same as mentioned in the description of the above Process 1.

This reaction is preferably conducted in a solvent such as acetic acid under heating.

(3) Process 3

The compound ($I^d$) can be prepared by subjecting the compound ($I^c$) to oxidative de-alkylation.

Preferred examples of the oxidizing agent to be used in the oxidative de-alkylation reaction may include a combination of osmic acid and perhalic acid or its salt (e.g. periodic acid, sodium periodate, perchloric acid, etc.), ozone, etc.

This reaction is preferably conducted in a solvent such as diethyl ether, dioxane, alcohol (e.g. methanol, ethanol, propanol, etc.), water or the like at around ambient temperature.

(4) Process 4

The compound ($I^f$) can be prepared by subjecting the compound ($I^e$) to elimination reaction of hydroxy protective group.

The reaction is carried out in the conventional manner, for instance, hydrolysis, reduction or the like.

The hydrolysis is preferably conducted in the presence of an acid or a base.

Preferred examples of the acid may include inorganic acids (e.g. chloric acid, hydrobromic acid, sulfuric acid, etc.), organic acids (e.g. formic acid, acetic acid, trifluoroacetic acid, propionic acid, benzenesulfonic acid, p-toluenesulfonic acid, etc.), and acidic ion-exchange resins.

Preferred examples of the base may include the same as mentioned in the description of the above Process 1.

The hydrolysis is conducted under comparatively mild conditions, under cooling or warming, in a solvent inert to the reaction [for example, a hydrophilic solvent such as water or alcohol (e.g. methanol, ethanol, propanol, etc.); acetone, N,N-dimethylformamide, tetrahydrofuran, dioxane, dimethyl sulfoxide or a mixture thereof; a hydrophobic solvent such as benzene or diethyl ether; etc. ]. Among them, those acids or bases which are liquid may serve also as solvents.

(ii) Reduction:

The reduction including chemical reduction and catalytic reduction is conducted in the conventional manner.

Preferred examples of the reducing agent to be used in the chemical reduction may include a combination of a metal (e.g. tin, zinc, iron, etc.) or a metallic compound (e.g. chromium chloride, chromium acetate, etc.) and an organic or inorganic acid ((e.g. formic acid, acetic acid, propionic acid, trifluoroacetic acid, p-toluenesulfonic acid, hydrochloric acid, hydrobromic acid, etc.).

Preferred examples of the catalyst to be used in the catalytic reduction may include platinum catalysts (e.g. platinum plate, platinum sponge, platinum black, platinum colloid, platinum oxide, platinum wire, etc.), palladium catalysts (e.g. palladium sponge, palladium black, palladium oxide, palladium-on-carbon, palladium colloid, palladium-barium sulfate, palladium-barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper), and the like.

The reduction is usually carried out in a solvent. Preferred solvents are, for example, water, alcohol (e.g. ethanol, propanol, etc.) and other usual organic solvents, and mixtures thereof. The above-mentioned liquid acids used in the chemical reduction may also serve as solvents. In the catalytic reduction, there may be exemplified as preferred solvents, diethyl ether, dioxane, tetrahydrofuran, etc. and mixtures thereof as well as the above-mentioned solvents.

This reaction is usually carried out under ice-cooling, at ambient temperature or under reflux, or at an intermediate temperature.

(5) Process 5

The compound ($I^h$) can be prepared by reacting the compound ($I^g$) with a halocarbonic acid lower alkyl ester.

Preferred examples of the lower alkyl halocarbonate may include methyl chlorocarbonate, ethyl chlorocarbonate, methyl bromocarbonate, ethyl bromocarbonate and the like. This reaction is preferably carried out in the presence of a base.

Preferred examples of the base may include the same as those mentioned in the description of the above Process 1.

This reaction is preferably conducted in a solvent such as tetrahydrofuran, under ice-cooling or at ambient temperature.

(6) Process 6

The compound ($I^i$) can be prepared by reacting the compound ($I^h$) with an oxidizing agent.

Preferred examples of the oxidizing agent may include Jones reagent, chromic acid, potassium permanganate and the like.

This reaction is preferably conducted in a solvent inert to the reaction, such as acetone, dimethylformamide, or methylene chloride, under cooling or at ambient temperature.

(7) Process 7

The compound ($I^j$) or its salt can be prepared by subjecting the compound ($I^i$) or its salt to de-esterification.

Preferred examples of salts of the compounds ($I^i$) and ($I^j$) may include the same as those of the compound (I).

The de-esterification reaction is conducted by the conventional method such as hydrolysis or reduction in the same manner as in the above Process 4.

(8) Process 8

The compound ($I^l$) can be prepared by reacting the compound ($I^k$) or its salt with an alkylating agent.

Preferred examples of salts of the compound ($I^k$) may include the same as those of the compound (I).

Preferred examples of the alkylating agent may include diazoalkanes (e.g. diazomethane, diazoethane, etc.), alkyl halides (e.g. methyl iodide, ethyl iodide, etc.), dialkyl sulfates (e.g. dimethyl sulfate, etc.) and the like.

This reaction is preferably conducted in a solvent inert to the reaction, such as water, acetone or alcohol (e.g. methanol, ethanol, propanol, etc.) at ambient temperature or the like.

In some cases, this reaction is preferably carried out in the presence of a base. Preferred examples of the base may include the same as those mentioned in the description of the above Process 1.

(9) Process 9

The compound ($I^n$) can be prepared by reacting the compound ($I^m$) with a halogenating agent.

Preferred examples of the halogenating agent may include halogens (e.g. chlorine, bromine, etc.), sulfuryl halogenides (e.g. sulfuryl chloride, etc.), thionyl halogenides (e.g. thionyl chloride, etc.), and the like.

This reaction is preferably conducted in a solvent such as methylene chloride, carbon tetrachloride, dioxane, or water, at ambient temperature or under heating up to the refluxing temperature.

(10) Process 10

The compound ($I^o$) or its salt can be prepared by reacting the compound ($I^j$) or its salt with a compound of the formula : $R_c^4$—OH wherein $R_c^4$ is as defined above, or its reactive derivative.

Preferred examples of salt of the compound ($I^o$) may include the same as those of the compound (I).

Said reactive derivative may include acid halides, acid azides, acid anhydrides, active amides, active esters and the like.

When a free carboxylic acid is used, this reaction is preferably conducted in the presence of a conventional condensing agent.

This reaction is preferably conducted in a conventional solvent such as methylene chloride, under ice-cooling or at ambient temperature, and good results are obtained in most cases when this reaction is carried out in the presence of a base such as pyridine. Those bases which are liquid may serve also as solvents.

(11) Process 11

The compound ($I^p$) can be prepared by reacting the compound ($I^s$) or its salt with a reducing agent.

In this process, the compound ($I^p$) can be prepared (1) by reacting the compound ($I^s$) or its salt directly with a reducing agent such as lithium alminium hydride, or, more preferably, (2) by reacting the compound ($I^s$) or its salt with a carboxy-activating agent such as an alkyl halocarbonate (e.g. methyl chlorocarbonate, ethyl chlorocarbonate, etc.) and then with a reducing agent such as alkaline metal borohydride (e.g. lithium borohydride, lithium cyanoborohydride, sodium borohydride, potassium borohydride, sodium cyanoborohydride, etc.).

This reaction is conducted in a conventional solvent such as methanol, ethanol, dioxane or tetrahydrofuran under ice-cooling, at ambient temperature, or at an intermediate temperature.

In the latter method (2), good results are obtained in most cases when the reaction is carried out in the presence of a base. Preferred examples of the base may include the same as mentioned in the description of the above Process 1.

In this process, the carboxy group of the compound ($I^{2o}$) reduced to the corresponding hydroxymethyl group to give the compound ($I^p$). However, when the latter method; namely, method (2), is employed, a compound ($I^p$) wherein $R_b^4$ is a hydrogen atom as resulting from the elimination of the lower alkanoyl for $R_c^4$ of the compound ($I^{2o}$) and a compound ($I^p$) wherein $R_b^4$ is a lower alkanoyl group with said group being retained may simultaneously be prepared in some cases depending on the reaction conditions.

(12) Process 12

The compound ($I^q$) can be prepared by reacting the compound ($I^p$) with a compound of the formula: $R_c^1$—OH wherein $R_c^1$ is as defined above, or its reactive derivative.

This reaction is conducted in substantially the same manner as the above Process 10.

(13) process 13

The compound ($I^r$) can be prepared by subjecting the compound ($I^s$) or its salt to Curtius rearrangement followed by treatment of the product with an alcohol.

In this process, the compound ($I^s$) or its salt is first reacted with a carboxy-activating agent, such as an alkyl halocarbonate (e.g. ethyl halocarbonate, etc.), in a solvent, such as acetone, in the presence of a base, such as trimethylamine, for activating the carboxy group, and then reacted with an alkali metal azide (e.g. sodium azide, etc.). After treatment with heating, the reaction product is treated with an alcohol (e.g. methanol, ethanol, etc.) to give the compound ($I^r$).

(14) Process 14

The compound ($I^u$) or its salt can be prepared by the following methods. Namely, the compound (III) is first reacted (1) with an oxidizing agent so as to convert the ethylenic double bond to the corresponding epoxide, and then (2) with malonic acid or its derivative at the carboxy groups in the presence of a base.

Preferred examples of salts of the compound ($I^u$) may include the same as those of the compound (I).

The oxidizing agent to be used in this reaction is a conventional oxidizing agent capable of converting an ethylenic double bond to the corresponding epoxide and may include, as preferred examples, organic peracids and salts thereof, such as perbenzoic acid, o-, m- or p-chloroperbenzoic acid, etc.

This reaction is conducted in a solvent, such as methylene chloride, water, methanol or ethanol, at around ambient temperature.

The reaction product (epoxide compound) thus produced is, with or without isolation thereof, reacted with malonic acid or its derivative at the carboxy groups in the presence of a base.

Preferred examples each of derivatives at the carboxy groups of malonic acid and the base are those mentioned in the description of the above Process 1.

The reaction in step (2) of this process is conducted in substantially the same manner as that in the above Process 1.

(15) Process 15

The compound ($I^v$) or its salt can be prepared by the following methods. Namely, (1) the compound (III) is reacted with an oxidizing agent so as to convert the ethylenic double bond to the corresponding epoxide, (2) the resulting epoxide is reacted with malonic acid or its derivative at the carboxy groups in the presence of a base, (3) the product, without isolation thereof, is reacted with formalin in the presence of a base, (4) the resulting product is reacted with an oxidizing agent such as Jones reagent, and (5) the reaction product is reacted with an oxidizing agent such as osmic acid plus periodic acid or its salt to give the compound ($I^v$).

The reactions in the above steps (1) and (2) are substantially the same as those mentioned in the description of the above Process 14, the reaction in step (3) is substantially the same as that mentioned in the description of the above Process 2, the reaction in step (4) is substantially the same as that mentioned in the description of the above Process 6, and the reaction in step (5) is substantially the same as that mentioned in the description of the above Process 3, and each reaction can be conducted in the same manner as the corresponding one mentioned earlier.

(16) Fermentation Process 16

FR-51785 substance can be produced by culturing an FR-51785 substance-producing strain of the genus Chaetomella in a nutrient medium.

The strain of *Chaetomella raphigera* which is employed as one of FR-51785 substance-producing strain belonging to the genus Chaetomella in accordance with this invention is a strain which the present inventors isolated from a soil sample collected in Fukuoka City, Japan (this strain is designated herein as Strain No. 3681), and has the following microbiological characteristics.

This strain does not produce a sexual reproductive organ on media but gives pycnidia with a raphae. The morphologic features of this asexual reproductive organ suggest that the strain belongs to the genus Chaetomella, fungi imperfecti. The morphological, cultural and physiological characteristics of this strain are as follows.

The pycnidia have no ostioles but a raphae for the conidia to ooze out, and have setae. These pycnidia measure 190 to 290 by 100 to 190 microns, oval to reniform, and dark brown in color. The raphae consists of 2 to 5 layers of thin-walled cells in rows, surrounded by thickened cells, and is situated in the upper half of the pycnidium along its major axis. The conidia ooze out as the result of maturation of the pycnidium and the consequent rupture of the thin-walled cells. The seta rises up vertically from the superficial cells of the pycnidium and is either L-configured or shaped like a golf club, measuring 30 to 60 by 3 to 4 microns. Its apex is somewhat enlarged, 6 microns in diameter and pale-colored, although the base of the seta is brown-colored. The setae are distributed over the upper half to one-third of the pycnidium at an interval of about 30 microns between septae and rarely overlapped.

Conidia are formed blastically from the conidiophore within the pycnidium. The condiophore is multi-cellular and irregularly branched, measuring 50 to 110 microns long and 1.5 to 2 microns wide, filiform (thread-like) and colorless. Conidia are produced apically on the conidophores (at the apex of apical cells and immediately beneath the septate wall of other cells), although the single terminal cell (30 to 70×1 to 1.5 microns) at the tip of the cell row forming the major axis of the condiophore is sterile. The conidia are oblong to boat-shaped or allantoid, unicellular, 6 to 8 by 2 to 2.5 microns, colorless and smooth.

This strain produces sporodochia, similar to those of Hainesia, in conjunction with pycnidia on various media, although in a number considerably less than that of pycnidia. The sporodochia are ampule- to flask-shaped, yellowish orange or pale orange, and terminating in a conidial mass. While setae are appended in the apical region, the cells on the surface of the sporodochia are not as much developed as the pycnidium. The features of the conidiophores constituting these sporodochia and of the conidia-forming cells, conidial cells, conidia, setae, etc., thereof are exactly the same as those of the pycnidium.

Growth on malt extract agar is rapid and expanding (colonies 7.0 cm dia. after 2 weeks at 25° C.). The colony is thin, somewhat downy and yellow-brown to dark brown. Black or dark brown pycnidia and orange-colored sporodochia are scattered on the surface of the medium. Growth on oatmeal agar is rapid (colonies 7.5 cm dia. under the same conditions as above), giving very flat and subhyaline to white colonies, with immersed vegetative mycelium. A large number of sporodochia, pale orange with a tinge of yellow, are observed in the center of the colony, together with a rather small number of pycnidia, although a large number of bare pycnidia appear in dots in the marginal area of the colony.

The temperature range for growth of this strain is 9° to 39° C. and the optimum temperature range is 27° to 31° C. (as measured with the temperature gradient shake incubator of Toyo Scientific Industries Model TN-3). The pH range for growth is pH 2 to 7 and the optimum range is pH 6 to 7 (malt extract/yeast extract liquid medium, shake culture at 25° C. for 7 days).

Based on the above characteristics in comparison with A. C. Stolk's description in Transactions of the British Mycological Society 46, 3, p. 413 (1963), this strain is identified to be *Chaetomella raphigera* Swift.

This *Chaetomella raphigera* Swift No. 3681 strain has been with the following International Depositary Authority under the Budapest Treaty: Fermentation Research Institute of the Agency of Industrial Science and Technology.

Identification number: FERM BP-293
Address: 1-3, Higashi 1 chome Yatabe-machi Tsukuba-gun Ibaraki-ken 305, Japan It is to be noted that for the production of the FR-51785 substance, this invention is not limited to the use of the particular organism as described above which is given for illustrative purpose only.

This invention also includes the use of any mutants which are capable of producing the FR-51785 substance, including natural mutants which are produced by natural mutation of the organism as well as artificial mutants which can be produced from the described organism by conventional means, such as X-rays, ultra-violet radiation, nitrogen mustard oils and the like.

The FR-5178 substance is produced when an FR-51785 substance-producing strain belonging to the genus Chaetomella is grown in a nutrient medium containing sources of assimilable carbon and nitrogen under aerobic conditions (e.g. shaking culture, submerged culture, etc.). The medium may be either synthetic, semi-synthetic or natural.

Preferred carbon sources may be glucose, mannose, glycerin, molasses, starch, starch hydrolysate and so on, and preferred nitrogen sources may be meat extract, casein hydrolysate, peptone, gluten meal, corn meal, cottonseed meal, soybean meal, corn steep liquor, dried yeast, ammonium phosphate, ammonium sulfate, urea and so on. There may also be incorporated inorganic salts such as the phosphates, chlorides and other salts of metals, e.g. disodium hydrogen phosphate, potassium dihydrogen phosphate, calcium carbonate, ferrous sulfate magnesium sulfate, copper sulfate, zinc sulfate, manganese chloride, magnesium chloride, etc. If copious foaming is encountered during fermentation, a defoaming agent such as vegetable oils, e.g. soybean oil, linseed oil, etc., higher alcohols, e.g. octadecanol, may be added in suitable amounts.

The fermentation is preferably conducted at around 30° C. for 50 to 100 hours.

From the above-mentioned fermentation conditions, the optimum set of conditions is selected according to the characteristics of the strain of microorganism employed.

Since a major portion of the FR-51785 substance thus produced in the culture broth is present extracellularly, the cells are first removed from the broth by centrifugation or filtration and the desired compound is then separated and purified from the supernatant or filtrate by the procedure employed commonly in the production of antibiotics in general. for example, there may be employed such procedures as concentration under reduced pressure, freeze drying, solvent extraction, pH adjustment, treatment with an anion exchange resin, cation exchange resin, nonionic adsorbent resin, etc., treatment with an adsorbent agent such as activated carbon, silicic acid, silica gel or alumina, crystallization, and recrystallization, either singly or in an optional combination.

The FR-51785 substance produced in the culture broth can be isolated in its free form or if desired, in the form of a salt. For isolating the substance in the form of a salt, the filtrate of the broth or a concentrate thereof is treated with a base such as an organic base, e.g. an alkali metal compound (e.g. sodium hydroxide, potassium hydroxide, etc.), an alkaline earth metal compound (e.g. calcium hydroxide, magnesium hydroxide, etc.), an inorganic base, e.g. ammonia, etc., an organic base (e.g. triethylamine, dicyclohexylamine, etc.) or an acid such as an inorganic acid (e.g. hydrochloric acid, sulfuric acid,phosphoric acid, etc.) or an organic acid (e.g. formic acid, acetic acid, p-toluenesulfonic acid, citric acid, oxalic acid, etc.), whereby the corresponding salt of FR-51785 substance can be obtained.

The salt of FR-51785 substance thus obtained can be reconverted to free FR-5178 substance in the per se conventional manner.

The FR-51785 substance has the following physico-chemical properties.

1. Molecular weight 248 (Mass spectrometry).
2. Elemental analysis (%) C: 63.13, H: 4.98.
3. Melting point 177°–179° C.
4. Specific rotation
   $[\alpha]_D^{25}$ +2.9 (c=1.0, ethanol).
5. Ultraviolet absorption spectrum:

| methanol $\lambda$ max | 285 nm ($E_{cm}^{\%}$720) |
|---|---|
| alkaline $\lambda$methanol max | 320 nm ($E_{cm}^{\%}$600) |

6. Infrared absorption spectrum $\nu_{max}^{nujol}$ 685, 880, 1035, 1060, 1100, 1160, 1300, 1390, 1490, 1710 (shoulder), 1735, 2800–3400 (broad), 3500 cm$^{-1}$.
7. $^1$H-Nuclear magnetic resonance spectrum $\delta_{TMS}^{CD3OD}$ 1.40–2.0 (1H, m), 2.1–2.8 (3H, m), 5.50 (1H, dd, J=8.0, Hz, 2.0Hz), 7.40 (3H, m), 7.75 (2H, m).
8. 13$_c$-Nuclear magnetic resonance spectrum $\delta_{TMS}^{CD3OD}$ 176.2(s), 171.0(s), 139.1(s), 131.7(s), 130.8(s), 129.6(d)x3, 128.4(d)x2, 79.2(d), 30.6(t), 29.8(t). 9. Color reactions: Positive: ferric chloride, iodine, cerium sulfate reactions. Negative: Ninhydrin, Molisch, Ehrlich and Dragendorff reactions.
10. Solubility: Soluble: methanol, acetone, ethyl acetate, ether. Insoluble: benzene, hexane, water.

Based on the above physicochemical properties and results of other studies, the following planochemical structure has been elucidated for FR-51785 substance.

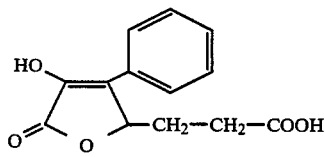

FR-51785 substance 3-(4-Hydroxy-5-oxo-3-phenyl-2,5-dihydro-2-furyl)propionic acid The compounds (II) and (III) to be used as the starting compounds in this invention are novel compounds and can be prepared as described in the working examples to be mentioned later or by a method analogous thereto.

The new furanone derivatives (I) obtainable by the foregoing processes include steroisomers due to asymmetric carbon within their molecule, all of such steroisomers falling within the scope of the invention.

The new furanone derivatives (I) and their pharmaceutically acceptable salts have been found to possess aldose reductase-inhibiting activity and are of value, for example as drugs for the treatment of diabetic cataract and neuropathy.

The aldose reductase-inhibiting activity values of some representative species of the furanone derivatives (I) are given below.

| (1) | Enzymatic assay method: | |
|---|---|---|
| | 0.5 M Phosphate buffer (pH 6.2) | 0.1 ml |
| | 2.0 M Lithium sulfate | 0.2 ml |
| | The compound of this invention (dissolved in physiological saline solution) | 0.1 ml |

-continued

| Enzyme solution [aldose reductase solution, prepared as described below (2)] | 0.5 ml |
|---|---|
| 60 mM D,L—glyceraldehyde | |
| 2.5 mM Nicotineamide adenine dinucleotide phosphate (reduced form) (NADPH) | 0.1 ml |

The above reactants were mixed and reacted at 35° C. for 2 minutes and the decrease in amount of NADPH was measured with an Automatic Reaction Rate Analyzer Model LKB-8600 of LKB Producter A. B. The enzyme activity at a change in absorbance of 0.001 per minute was taken as unity. (2) Method for preparing an enzyme solution Rabbit eyes were enucleated and the lenses collected. The lenses were homogenized with 3 volumes of distilled water at 4° C. (All the subsequent procedures were also performed at 4° C.) and centrifuged at 10,000 G for 60 minutes. The supernatant was dialyzed against 2 liters of 0.05M of saline solution and the interal fluid was used as the enzyme solution.

The results are shown in the following table. Each IC$_{50}$ value (μg/ml) represents the concentration of the compound of this invention at which the aldose reductase activity is inhibited by 50%.

| Compound (No. of Example) | IC$_{50}$ (μg/ml) |
|---|---|
| 10 | 0.021 |
| 11 | 0.19 |
| 12 | 0.10 |
| 18 | 0.06 |
| 19 | 0.25 |
| 20 | 0.04 |
| 21 | 0.04 |

The new furanone derivatives (I) and their pharmaceutically acceptable salts of this invention can be used as pharmaceutical compositions for the treatment of diabetic cataract and/or neuropathy. The pharmaceutical composition is provided in various forms such as solid preparations, semi-solid preparations or liquid preparations, which contain the active compound of this invention, i.e., the compound (I) or a pharmaceutically acceptable salt thereof, together with an organic or inorganic carrier or/and excipient suitable for external, internal or local administration. This active component is used in combination with harmless and pharmacologically acceptable auxiliary components to provide such suitable dosage forms as tablets, pellets, capsules, suppositories, solutions, emulsions, suspensions, etc. Examples of such auxiliary components include those which can be effectively utilized in the production of solid, semisolid or liquid preparations, for example, water, glucose, lactose, gelatin, mannitol, starch paste, magnesium trisilicate, corn starch, keratin, colloidal silica, potato starch, urea, etc. Furthermore, such auxiliaries as stabilizers, extenders, colorants and fragrances may also be incorporated. The pharmaceutical compositions according to this invention may also contain preservatives so that the activity of the active component can be preserved. Said compositions should contain the active component in an amount sufficient for the production of desirable therapeutic effects against the progress or actual condition of a disease concerned.

When the pharmaceutical compositions are applied to humans, they are desirably administered by the intravenous, intramuscular or oral route. The effective dose of each active substance depends on the age and/or symptom of the patient to be treated. Generally, however, the pharmaceutical preparations contain about 50 mg, 100 mg, 250 mg or 500 mg of the active substance per unit dosage form and are administered to humans or animals at a daily dose of 0.1–100 mg per kilogram of body weight.

The following examples illustrate this invention.

PREPARATION 1

To a suspension of sodium hydride (50%; 0.6 g) (deprived of mineral oil) in tetrahydrofuran (10 ml), there was added dropwise a solution of 5-phenyl-4-pentenol [1.66 g; known compound; cf. e.g. Journal of the Chemical Society, page 1863 (1961)] in tetrahydrufuran (10 ml) in argon atmosphere at room temperature. The mixture was stirred at the same temperature for 5 minutes. A solution of benzyl bromide (1.93 g) in tetrahydrofuran (10 ml) was added dropwise and the mixture was stirred at the same temperature for 20 hours. The tetrahydrofuran was distilled off under reduced pressure and water was added to the residue, followed by extraction with ether. After washing with water and drying over magnesium sulfate, the solvent was distilled off, and the residue was subjected to silica gel chromatography, elution being carried out with chlorofrom to give 5-benzyloxy-1-phenyl-1-pentene (2.5 g) as a colorless oil.

I.R. (chloroform) : 1600, 1100, 965, 695 cm$^{-1}$.

N.M.R. (CDCl$_3$ $\delta$): 7.23 (10H, s), 6.5–6.1 (2H, m), 4.47 (2H, s), 3.47 (2H, t), 2.43–2.13, (2H, m), 2.00–1.63 (2H, m).

PREPARATION 2

5-Benzyloxy-1-phenyl-1-pentene (1.8 g) was dissolved in methylene chloride (50 ml) and, with stirring at room temperature, a solution of m-chloroperbenzoic acid (80%; 1.8 g) in methylene chloride (20 ml) was added dropwise. The mixture was stirred at the same temperature for 2.5 hours, and the reaction mixture was washed with 10% aqueous sodium hydrogen sulfite, 5% aqueous sodium bicarbonate and water in that order and dried over magnesium sulfate. The solvent was then distilled off to give 2-(3-benzyloxypropyl)-1-phenyloxirane (1.9 g) as a colorless oil.

I.R. (chloroform): 1110, 695 cm$^{-1}$.

N.M.R. (CDCl$_3$, $\delta$):7.27 (10 H, s), 4.50 (2H, s), 3.70–3.40 (3H, m), 3.10–2.83 (1H, m) 2.00–1.73 (4H, m).

PREPARATION 3

In an argon atmosphere, butyllithium (10%; 37 ml) was added dropwise to a suspension of (4-chlorobenzyl)triphenylphosphonium chloride (24 g) in tetrahydrofuran (70 ml) with ice-cooling and stirring. After stirring at the same temperature for 30 minutes, a solution of 4-tetrahydropyranyloxy-1-butanal (9 g) in tetrahydrofuran (30 ml) was added dropwise, and the mixture was stirred at room temperature for 2 hours. The tetrahydrofuran was distilled off under reduced pressure and water was added to the residue, followed by extraction with petroleum ether. After washing with water and drying over magnesium sulfate, the solvent was distilled off, and the residue was subjected to silica gel column chromatography, elution being carried out with chloroform to give 1-(4-chlorophenyl)-5-(2-tetrahydropyranyloxy)-1-pentene (7 g) as a light-yellow oil.

I.R. (chloroform): 1590, 1490, 1130 cm$^{-1}$.

N.M.R. (CDCl$_3$, $\delta$):7.20 (4H, s), 6.44–6.00 (2H, m), 4.64–4.44 (1H, m), 3.92–3.60 (2H, m), 3.60–3.28 (2H, m), 2.48–2.12 (2H, m), 2.00–1.40 (8H, m).

EXAMPLE 1

In a nitrogen atmosphere, dimethyl malonate (3 g) was added dropwise to a sodium ethoxide-ethanol solution [prepared from sodium (0.5 g) and ethanol (35 ml)] with stirring at room temperature. With stirring under reflux, a solution of 2-(3-benzyloxypropyl)-1-phenyloxirane (1.9 g) in ethanol (15 ml) was added dropwise. After stirring under reflux for 20 hours, the reaction mixture was returned to room temperature. A 20% aqueous sodium hydroxide solution (15 ml) was added and the mixture was stirred under reflux for 2 hours. The ethanol was distilled off under reduced pressure, and the residue was shaken with water and ether. The organic layer was extracted with a 5% aqeuous sodium hydroxide solution, and the aqueous layers were combined, acidified with hydrochloric acid and extracted with ether. After washing with water and drying over magnesium sulfate, the solvent was distilled off to give 5-(3-benzyloxypropyl)-2-oxo-4-phenyltetra-hydro-3-furancarboxylic acid (2.0 g) as a colorless oil.

I.R. (chloroform): 3600–2300, 1777, 1720, 695 cm$^{-1}$.

N.M.R. (CDCl$_3$, $\delta$):7.23 (10H, s), 6.30 (1H, s, disappearing upon addition of heavy water), 5.07–4.73 (1H, m), 4.40 (2H, s), 4.30–3.87 (2H, m), 3.50–3.30 (2H, t), 2.00–1.10 (4H, m).

EXAMPLE 2

5-(3-Benzyloxypropyl)-2-oxo-4-phenyltetrahydro-3-furancarboxylic acid (1 g) was dissolved in a solution (5 ml) prepared from sodium acetate (105 mg), acetic acid (4 ml), formalin (2.92 ml) and diethylamine (1 ml), and the solution was heated on a water bath (100° C.) for 30 minutes. After cooling, the reaction mixture was poured into ice water and extracted with ether. The extract was washed with 5% sodium bicarbonate and water and dried over magnesium sulfate. The solvent was then distilled off to give 5-(3-benzyloxypropyl)-3-methylene-4-phenyltetrahydro-2-furanone (0.7 g) as a colorless oil.

I.R. (chloroform): 1760, 1110, 700 cm$^{-1}$.

N.M.R. (CDCl$_3$, $\delta$):7.23 (10H, s), 6.40 (1H, d, J=2 Hz), 5.58 (1H, d, J=2 Hz), 4.90–4.53 (1H, m), 4.37 (2H, s), 4.37–4.22 (1H, m), 3.47–3.37 (2H, t, J=6 Hz), 1.87–1.10 (4H, m).

EXAMPLE 3

5-(3-Benzyloxypropyl)-3-methylene-4-phenyltetrahydro-2-furanone (0.6 g) was dissolved in dioxane (7 ml)-water (3 ml) and, with stirring at room temperature, osmic acid (15 mg) was added, followed by stirring at the same temperature for 5 minutes. To the mixture was added sodium periodate in small installments over 15 minutes, and the mixture was stirred at room temperature for 4.5 hours. The reaction mixture was poured into ice water (30 ml), extracted with ether, and washed with water. After drying over magnesium sulfate, the solvent was distilled off, and the residue was subjected to silica gel chromatography, elution being carried out with chloroform. The crude crystals thus obtained were recrystallized from ether to give 5-(3-benzyloxypropyl)-3-hydroxy-4-phenyl-2(5H-furanone (250 mg) as colorless prisms. m.p. 120°–122.5° C.

I.R. (chloroform): 3500, 1740, 690 cm$^{-1}$.

N.M.R. (CDCl$_3$, δ):7.73–7.20 (10H, m), 5.53–5.33 (1H, m , 4.43 (2H, s), 3.50 (2H, t), 2.40–1.50 (4H, m).

EXAMPLE 4

5-(3-Benzyloxypropyl)-3-hydroxy-4-phenyl-2(5H)-furanone (65 mg) was dissolved in methanol (20 ml), and palladium black (20 mg) was added. Catalytic reduction was carried out in ordinary temperature and atmosphere. After completion of the reaction, the palladium black was filtered off and the methanol was distilled off under reduced pressure. The crude crystals thus obtained were recrystallized from chloroform to give 3-hydroxy-5-(3-hydroxypropyl)-4-phenyl-2(5H)-furanone (45 mg). m.p. 148°–150° C.

I.R. (nujol): 3450–2300, 1725 cm$^{-1}$.

N.M.R. (CD$_3$OD, δ):7.83–7.30 (5H, m), 5.48 (1H, dd), 3.50 (2H, t), 2.40–1.33 (4H, m).

EXAMPLE 5

3-Hydroxy-5-(3-hydroxypropyl)-4-phenyl-2(5H)-furanone (25 mg) was dissolved in tetrahydrofuran (6 ml), and triethylamine (0.018 ml) was added with ice-cooling and stirring, followed by dropwise addition of ethyl chlorocarbonate (0.012 ml). The mixture was stirred at the same temperature for 5 minutes, and the reaction mixture was acidified with hydrochloric acid and extracted with ethyl acetate. The extract was washed with water and dried over magnesium sulfate. The solvent was then distilled off. The remaining oil was purified by preparative thin layer chromatography (silica gel; developer: 4% methanol-chloroform) to give ethyl 5-(3-hydroxypropyl)-2-oxo-4-phenyl-2,5-dihydro-3-furancarboxylate (30 mg) as a colorless oil.

I.R. (chloroform): 1775, 1765, 1245 cm$^{-1}$.

N.M.R. (CDCl$_3$, δ): 7.47 (5H, s), 5.55 (1H, dd), 4.33 (2H, q, J=6 Hz), 3.65 (2H, t, J=6 Hz), 2.33–1.33 (4H, m), 1.37 (3H, t, J=6 Hz).

EXAMPLE 6

Ethyl 5-(3-hydroxypropyl)-2-oxo-4-phenyl-2,5-dihydro-3-furancarboxylate (20 mg) was dissolved in acetone (2 ml), and Jones reagent (0.05 ml) was added dropwise with ice-cooling and stirring. The mixture was stirred at the same temperature for 2 hours, and the reaction mixture was poured into ice water (15 ml) and extracted with ethyl acetate. The extract was washed with water and dried over magnesium sulfate. The solvent was then distilled off. The remaining oil was purified by preparative silica gel thin layer chromatography (eluent: 5% methanol-chloroform) to give 3-(4-ethoxycarbonyloxy-5-oxo-3-phenyl-2,5-dihydro-2-furyl)propionic acid (20 mg) as colorless prisms. m.p. 139°–141° C. (recrystallized from ether).

I.R. (chloroform): 3600–2400, 1750, 1710, 1240, 1210 cm$^{-1}$.

N.M.R. (CDCl$_3$, δ): 7.52 (5H, s), 6.76–6.28 (1H, m), 5.60 (1H, dd), 4.32 (2H, q, J=7 Hz), 2.80–2.20 (3H, m), 2.00–1.60 (1H, m), 1.36 (3H, t, J=7 Hz).

EXAMPLE 7

3-(4-Ethoxycarbonyloxy-5-oxo-3-phenyl-2,5-dihydro-2-furyl)propionic acid (20 mg) was dissolved in methanol (3 ml), and 10% aqueous potassium carbonate (3 ml) was added. The mixture was stirred at room temperature for 1 hour. The reaction mixture was poured into ice water (10 ml), acidified with hydrochloric acid and extracted with ethyl acetate. The extract was washed with water and dried over magnesium sulfate. The solvent was then distilled off. The remaining oil was purified by preparative silice gel thin layer chromatography (developer: 5% methanol-chloroform). Recrystallization from chloroform gave 3-(4-hydroxy-5-oxo-3-phenyl-2,5-dihydro-2-furyl)propionic acid (11 mg) as colorless needles. m.p. 177°–179° C.

I.R. (chloroform): 3600–2270, 1740 cm$^{-1}$.

N.M.R. (CD$_3$OD, δ): 7.88–7.32 (5H, m), 5.52 (1H, dd), 2.67–1.57 (4H, m).

EXAMPLE 8

1-(4-Chlorophenyl)-5-(2-tetrahydropyranyloxy)-1-pentene (1 g) was dissolved in methylene chloride (20 ml), and a solution of 3-chloroperbenzoic acid (80%; 0.85 g) in methylene chloride (10 ml) was added dropwise with stirring at room temperature. The mixture was stirred at the same temperature for 4 hours, washed with 10% aqueous sodium hydrogen sulfite, 5% aqueous sodium bicarbonate, and water in that order, and dried over magnesium sulfate. The solvent was then distilled off to give 1-(4-chlorophenyl)-2-[3-(2-tetrahydropyranyl)oxypropyl]oxirane (0.95 g). On the other hand, dimethyl malonate (1.5 g) was added dropwise to a sodium ethoxideethanol solution [prepared from metallic sodium (0.25 g) and absolute ethanol (20 ml)] with stirring at room temperature, and a solution of 1-(4-chlorophenyl)-2-[ 3-(2-tetrahydropyranyl)oxypropyl]oxirane (0.8 g) in ethanol (10 ml) was added dropwise with stirring under reflux on a water bath at 100° C. The mixture was stirred under reflux for 20 hours and then cooled, and a 15% aqueous sodium hydroxide solution was added, followed by stirring under reflux for 2 hours. After cooling, the ethanol was distilled off under reduced pressure, and the residue was shaken with water and ether. The organic layer was ectracted with 5% aqueous sodium chloride. The aqueous layer was acidified with hydrochloric acid and extracted with ether and the extract was washed with water and dried over magnesium sulfate. The solvent was then distilled off to give 4-(4-chlorophenyl)-5-(3-hydroxypropyl)-2-oxotetrahydro-3-furancarboxylic acid (640 mg) as a light-yellow oil.

I.R. (chloroform): 3600–2400, 1780, 1730 cm$^{-1}$.

EXAMPLE 9

4-(4-Chlorophenyl)-5-(3-hydroxypropyl)-2-oxotetrahydro-3-furancarboxylic acid (640 mg) was dissolved in a solution (5 ml) prepared from sodium acetate (105 mg), acetic acid (4 ml), formalin (2.92 ml) and diethylamine (1 ml), and the solution was heated on a water bath (100° C.) for 30 minutes. The reaction mixture was poured into ice water (20 ml) and extracted with ether. The extract was washed with 5% aqueous sodium hydroxide and water and dried over magnesium sulfate. The solvent was then distilled off. The residue was subjected to silical gel column chromatography, elution being carried out with chloroform to give 4-(4-chlorophenyl)-5-(3-hydroxypropyl)-3-methylenetetrahydro-2-furanone (512 mg) as a colorless oil.

I.R. (chloroform): 3350, 1755, 1660, 1600 cm$^{-1}$.

N.M.R. (CDCl$_3$, δ): 7.47–6.97 (4H, m), 6.43 (1H, d, J=2 Hz), 5.58 (1H, d, J=2 Hz), 4.93–4.60 (1H, m), 4.50–4.17 (1H, m), 3.93–3.33 (2H, m), 2.00–1.07 (4H, m).

EXAMPLE 10

4-(4-Chlorophenyl)-5-(3-hydroxypropyl-3-methylenetetrahydro-2-furanone (100 mg) was dissolved in acetone (2 ml), and Jones reagent (0.25 ml) was added dropwise with ice-cooling. The mixture was stirred at the same temperature for 2 hours, poured into ice water (20 ml) and extracted with ethyl acetate. The extract was washed with water and dried over magnesium slufate. The solvent was then distilled off to give crude 3-[3-(4-chlorophenyl)-5-oxo-4-methylenetetrahydro-2-furyl]-propionic acid (80 mg) as an oil. The above compound was dissolved in dioxane (5 ml)-water (2 ml), and osmic acid (10 mg) was added. The mixture was stirred at room temperature for 5 minutes. To the reaction mixture was added portionwise sodium periodate (500 mg), and the mixture was stirred at the same temperature for 4 hours, followed by addition of water (20 ml) and extraction with ethyl acetate. The extract was washed with water and dried over magnesium sulfate. The solvent was then distilled off and the residue was purified by preparative silica gel thin layer chromatography (developer: 10% methanol-chloroform) to give 3-[3-(4-chlorophenyl)-4-hydroxy-5-oxo-2,5-dihydro-2-furyl]propionic acid (20 mg) as colorless crystals. I.R. (chloroform): 3600–2350, 1740, 1595 cm$^{-1}$. N.M.R. (CD$_3$OD, δ): 7.75 (2H, d, J=8 Hz), 7.44 (2H, d, J=8 Hz), 5.48 (1H, dd), 2.53–2.13 (3H, m), 1.93–1.40 (1H, m).

EXAMPLE 11

1-(4-Fluorophenyl)-5-(2-tetrahydropyranyloxy)-1-pentene (6.7 g) was dissolved in methylene chloride (80 ml), and a solution of 3-chloroperbenzoic acid (80%; 6.5 g) in methylene chloride (40 ml) was added dropwise with stirring at room temperature. The mixture was stirred at the same temperature for 4 hours, washed with 10% aqueous sodium hydrogen sulfite, 5% aqueous sodium bicarbonate and water in that order and dried over magnesium sulfate. The solvent was then distilled off to give 6 g of a colorless oil. In a nitrogen atmosphere, dimethyl malonate (10 g) was added dropwise to a sodium ethoxide-ethanol solution [prepared from metallic sodium (1.7 g) and absolute ethanol (70 ml)] with stirring at room temperature. With stirring under reflux on a water bath at 100° C., a solution of the above-obtained oil (6 g) in ethanol (20 ml) was added dropwise and the mixture was stirred under reflux for 17 hours. After cooling, a 15% aqueous sodium hydroxide solution was added, and the mixture was stirred under reflux of 2 hours. After cooling, the ethanol was distilled off under reduced pressure, and the residue was shaken with water and ether. The organic layer was extracted with 5% aqueous sodium hydroxide, and the aqueous layer was acidified with hydrochloric acid and extracted with ether. The extract was washed with water and dried over magnesium sulfate. The solvent was then distilled off to give a yellow oil (1.8 g). This oil was dissolved in a solution (10 ml) prepared from sodium acetate (0.21 g), acetic acid (8 ml), formalin (5.84 ml) and diethylamine (2 ml), and the solution was heated on a water bath (100° C.) for 30 minutes. The reaction mixture was poured into ice water (40 ml), extracted with ether, washed with 5% aqueous sodium hydroxide and water in that order, and dried over magnesium sulfate. The solvent was then distilled off to give 4-(4-fluorophenyl)-5-(3-hydroxypropyl)-3-methylenetetrahydro-2-furanone (0.6 g) as an oil. This oil was dissolved in acetone (2 ml) and Jones reagent (2 ml) was added dropwise with ice-cooling. The mixture was stirred at the same temperature for 1 hour, poured into ice water (20 ml), and extracted with ethyl acetate. The extract was washed with water and dried over magnesium sulfate. The solvent was distilled off to give an oil (0.35 g). This oil (200 mg) was dissolved in dioxane (7 ml)-water (3 ml), and osmic acid (15 mg) was added. The mixture was stirred at room temperature for 5 minutes. To the reaction mixture was added portionwise sodium periodate (3 g), and the mixture was stirred at the same temperature for 3 hours, followed by addition of water (40 ml) and extraction with ethyl acetate. The extract was washed with water and dried over magnesium sulfate. The solvent was then distilled off and the residue was purified by silica gel chromatography (10% methanol-chloroform) to give 3-[3-4-fluorophenyl)-4-hydroxy-5-oxo-2,5-dihydro-2-furyl]propionic acid (30 mg) as colorless crystals.

I.R. (chloroform): 3600–2350, 1740, 1600 cm$^{-1}$.

N.M R. (CD$_3$OD, δ): 8.23–7.00 (4H, m), 5.48 (1H, dd), 2.76–1.43 (4H, m).

EXAMPLE 12

In substantially the same manner as Example 11, 3-[4-hydroxy-5-oxo-3-(3-trifluoromethylphenyl)-2,5-dihydro-2-furyl]propionic acid was obtained.

I.R. (chloroform): 3600–2350, 1740 cm$^{-1}$.

N.M.R. (CD$_3$OD, δ): 8.13–7.57 (4H, m), 5.55 (1H, dd), 2.67–1.57 (4H, m).

EXAMPLE 13

3-(4-Hydroxy-5-oxo-3-phenyl-2,5-dihydro-2-furyl)-propionic acid (100 mg) was dissolved in pyridine (2 ml), and acetic anhydride (1 ml) was added. The mixture was allowed to stand overnight. The excess reagent and solvent were removed by distillation under reduced pressure, and the residue was dried to give 3-(4-acetoxy-5-oxo-3-phenyl-2,5-dihydro-2-furyl)propionic acid (116 mg) as an oil.

I.R. (chloroform): 1765, 1705 cm$^{-1}$.

N.M.R. (CDCl$_3$, δ): 7.5 (5H, s), 6.3 (1H, m) 5.7 (1H, m), 2.8–1.8 (4H, m), 2.3 (3H, s).

EXAMPLE 14

3-(4-Acetoxy-5-oxo-3-phenyl-2,5-dihydro-2-furyl)-propionic acid (58 mg) was dissolved in acetone (2 ml), and a solution of triethylamine (32 μl) in acetone (5 ml) was added with ice-cooling. Then, a solution of ethyl chlorocarbonate (24 μl) in acetone (2 ml) was added dropwise slowly. The mixture was stirred with ice-cooling for 30 minutes, and a solution of sodium azide (19.5 mg) in water (1 ml) was added. The mixture was stirred with ice-cooling for 1 hour, poured into ice water, and extracted with ether. After removal of the ether by distillation, benzene (5 ml) was added, and the mixture was heated under reflux for 1 hour. After cooling, methanol (2 ml) was added, and the mixture was allowed to stand at room temperature overnight. The solvent was distilled off to give 56 mg of a crude product. This was subjected to preparative silica gel thin layer chromatography (0.5 mm×3, Merck) using chloroform-ethyl acetate (5:1) as the developing solvent to give methyl N-2-(4-acetoxy-5-oxo-3-phenyl-2,5-dihydro-2-furyl)ethylcarbamate (43 mg).

I.R. (chloroform): 1770, 1720 cm$^{-1}$.

N.M R. (CDCl$_3$, δ): 7.5 (5H, s), 5.56 (1H, dd, J=4.8 Hz), 5.16 (1H, m), 3.55 (3H, s), 3.35 (2H, m), 2.36 (3H, s), 2.23 (1H, m), 1.9 (1H, m).

EXAMPLE 15

3-(4-Acetoxy-5-oxo-3-phenyl-2,5-dihydro-2-furyl)-propionic acid (58 mg) was dissolved in a mixture of tetrahydrofuran (3 ml) and triethylamine (28 μl), and a solution of ethyl chlorocarbonate (19 μl) in tetrahydrofuran (1 ml) was added dropwise slowly at −5° C. over 10 minutes. The mixture was stirred at −5° C. for 30 minutes and filtered. To the filtrate was added a solution of sodium borohydride (23 mg) in water (1 ml) at 10° C. Then, the mixture was stirred at room temperature for 1.5 hours, acidified with cooled 1N hydrochloric acid, and extracted with ethyl acetate. After drying, the solvent was distilled off, and the residue was subjected to preparative silica gel thin layer chromatography (0.5 mm×4, Merck) using 35% ethyl acetate-chloroform as the developing solvent to give 3-hydroxy-5-(3-hydroxypropyl)-4-phenyl-2(5H)-furanone (Compound I, 10 mg) and 3-acetoxy-5-(3-hydroxypropyl)-4-phenyl-2(5H)-furanone (Compound II, 12 mg).

Compound I

N.M.R. (CDCl$_3$, δ): 7.7–7.3 (5H, m), 5.4 (1H, m), 3.55 (2H, m), 2.2–1.5 (4H, m).

Compound II

I.R. (chloroform): 1780, 1760, cm$^{-1}$.

N.M.R. (CDCl$_3$, δ): 7.5 (5H, s), 5.55 (1H, m), 3.65 (2H, m), 2.36 (3H, s), 2.2–1.5 (4H, m).

EXAMPLE 16

3-Hydroxy-5-(3-hydroxypropyl)-4-phenyl-2(5H)-furanone (8 mg) was dissolved in pyridine (1 ml), and acetic anhydride (0.5 ml) was added. The mixture was allowed to stand at room temperature overnight, and the excess reagent and solvent were removed by distillation to give 3-acetoxy-5-(3-acetoxypropyl)-4-phenyl-2(5H)-furanone (10 mg).

I.R. (chloroform): 1760, 1730 cm$^{-1}$.

N.M.R. (CDCl$_3$, δ): 7.5 (5H, s), 5.5 (1H, m), 4.0 (2H, s), 2.3 (3H, s), 1.95 (3H, s), 2.2–1.5 (4H, m).

EXAMPLE 17

3-Acetoxy-5-(3-hydroxypropyl)-4-phenyl-2(5H)-furanone was worked up in substantially the same manner as Example 16 to give 3-acetoxy-5-(3-acetoxypropyl)-4-phenyl-2(5H)-furanone.

I.R. (chloroform): 1760, 1730 cm$^{-1}$.

N.M.R. (CDCl$_3$, δ) : 7.5 (5H, s), 5.5 (1H, m), 4.0 (2H, s), 2.3 (3H, s), 1.95 (3H, s), 2.2–1.5 (4H, m).

EXAMPLE 18

3-(4-Hydroxy-5-oxo-3-phenyl-2,5-dihydro-2-furyl)-propionic acid (100 mg) was dissolved in methanol (2 ml), and a solution of diazomethane in ether was added thereto until the yellow color did not vanish any longer. The mixture was allowed to stand at room temperature overnight. The solvent was then distilled off to give methyl 3-(4-methoxy-5-oxo-3-phenyl-2,5-dihydro-2-furyl)propionate (110 mg).

I.R. (chloroform): 1750, 1730 cm$^{-1}$.

N.M.R. (CDCl$_3$, δ): 7.8–7.3 (5H, m), 5.5 (1H, dd, J=2.9 Hz), 4.1 (3H, s), 3.7 (3H, s), 2.6–1.6 (4H, m).

EXAMPLE 19

Methyl 3-(4-methoxy-5-oxo-3-phenyl-2,5-dihydro-2-furyl)propionate (110 mg) was dissolved in methylene chloride (10 ml), and sulfuryl chloride (2 ml) was added. The mixture was heated under reflux for 7 hours. After cooling, the reaction mixture was poured into ice water and extracted with chloroform. The chloroform solution was washed with water, aqueous sodium bicarbonate and aqueous sodium chloride in that order and dried. The solvent was then distilled off under reduced pressure to give a residue (145 mg). The residue was purified by preparative silica gel thin layer chromatography (0.5 mm×5, Merck) using 5% ethyl acetate-chloroform as the developing solvent to give methyl 3-(3,4-dichloro-4-methoxy-5-oxo-3-phenyl)propionate (110 mg).

I.R. (chloroform): 1810, 1735 cm$^{-1}$.

N.M.R. (CDCl$_3$, δ): 7.8–7.4 (5H, m), 5.6 (1H, dd, J=6.7 Hz), 4.0 (3H, s), 3.77 (3H, s), 2.9–2.2 (4H, m).

EXAMPLE 20

In substantially the same manner as Example 11, 3-[3-(3-chlorophenyl)-4-hydroxy-5-oxo-2,5-dihydro-2-furyl]propionic acid was obtained.

I.R. (CDCl$_3$): 3600–2350, 1740 cm$^{-1}$.

N.M.R. (CD$_3$OD, δ): 7.85–7.35 (4H, m), 5.50 (1H, m), 2.60–2.10 (3H, m), 1.93–1.40 (1H, m).

EXAMPLE 21

A medium (pH 6.0) containing 2% of oxidized starch, 1% of glucose, 2% of corn steep liquor, 3% of cottonseed meal, 0.5% of moratin and 0.2% of calcium carbonate was distributed in 100-ml portions into sixteen 500-ml Sakaguchi flasks and sterilized at 120° C. for 20 minutes. Thereafter, one loopful of a slant culture of *Chaetomella raphigera* Swift strain No. 3681 was used for inoculation of the contents of each flask, followed by shake culture at 28° C. for 2 days.

Separately, 160 liters of a medium (pH 6.0) containing 0.3% of oxidized starch, 2% of glucose, 3% of corn steep liquor, 1% of peanut meal, 0.5% of moratin and 0.2% of calcium carbonate was poured into a 200-liter jar fermenter. After sterilization at 120° C. for 20 minutes, inoculation was conducted using the whole amount of the above culture and then incubation was conducted at 28° C. for 4 days.

To the culture broth after incubation, 4 kg of Radiolite was added. Filtration gave 120 liters of a filtrate. This filtrate was treated on a Diaion HP-20 (trademark, Mitsubishi Chemical Industries; macroporous nonionic adsorbent resin) column (20 l ) for adsorption of an active substance. The column was washed with 60 liters of water and then the active substance was eluted with 80 liters of methanol. The eluate was concentrated under reduced pressure and made into an aqueous solution (8 liters). This aqueous solution was adjusted to pH 9.0 and treated with 8 liters of ethyl acetate for transfer of impurities to the solvent layer. The aqueous layer was adjusted to pH 2.0 and extracted with two 8-liter portions of ethyl acetate for transfer of the active substance to the solvent layer. The solvent layer was concentrated, mixed with Silical CC-4 (trademark, Mallinckrodt), and submitted to a one-liter Silical CC-4 column (packed with hexane). The active substance was eluted with a hexane-ethyl acetate (1:1) mixture. The eluate was concentrated and again submitted to a 300-ml Silical CC-4 column. The active substance was eluted with a chloroform-methanol (50:1) mixture, and the eluate was concentrated to dryness. The thus-obtained oily substance was crystallized with ether-benzene to give 1.6 g of FR-51785 substance as colorless crystals.

We claim:

1. A compound of the following formula or its pharmaceutically acceptable salt:

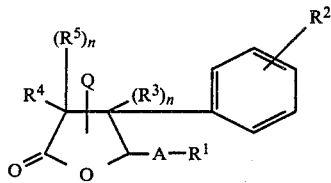

wherein A is a lower alkylene group; $R^1$ is a carboxy, hydroxy, lower alkoxycarbonyl, lower alkoxycarbonylamino phenyl(lower)alkyloxy, benzoloxy, or lower alkanoyloxy group; $R^2$ is a hydrogen or halogen atom or a halo(lower)alkyl group; $R^3$ is a hydrogen or halogen atom; $R^4$ is a hydroxy, lower alkoxy, lower alkanoyloxy or lower alkoxycarbonyloxy group and $R^5$ is a hydrogen or halogen atom; Q is the number of double bonds which is equal to 0 or 1; n is an integer of 0 or 1, provided that when Q is 0, n is 1 and when Q is 1, n is 0.

2. A pharmaceutical composition of aldose reductase inhibitory activity comprising an effective amount of a compound as defined in claim 1 or its pharmaceutically acceptable salt in admixture with a substantially non-toxic carrier or excipient.

3. A method comprising administering an effective amount of a compound or its pharmaceutically acceptable salt to a subject in need of treatment of diabetic cataract and/or neuropathy, said compound being of the formula:

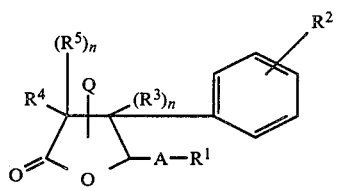

wherein

A is a lower alkylene group;

$R^1$ is a carboxy, hydroxy, lower alkoxycarbonyl, lower alkoxycarbonylamino, phenyl(lower)alkyloxy, benzoyloxy or lower alkanoyloxy group;

$R^2$ is a hydrogen or halogen atom or a halo(lower)alkyl group;

$R^3$ is a hydrogen or halogen atom;

$R^4$ is hydroxy, lower alkoxy, lower alkanoyloxy or lower alkoxycarbonyloxy group; and $R^5$ is a hydrogen or halogen atom;

Q is the number of double bonds which is equal to 0 or 1;

n is an integer of 0 or 1, provided that when Q is 0, n is 1 and when Q is 1, n is 0.

4. A compound according to claim 1, which is 3-(4-hydroxy-5-oxo-3-phenyl-2,5-dihydro-2-furyl) propionic acid.

* * * * *